(12) United States Patent
Schalapski et al.

(10) Patent No.: US 8,664,444 B2
(45) Date of Patent: Mar. 4, 2014

(54) METHOD FOR PRODUCING PRIMARY ALIPHATIC AMINES FROM ALDEHYDES

(75) Inventors: Kurt Schalapski, Oberhausen (DE); Norman Nowotny, Essen (DE); Matthias Eisenacher, Wesel (DE); Dirk Bermann, Mülheim (DE); Thorsten Kreickmann, Oberhausen (DE); Peter Heymanns, Essen (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 13/817,155

(22) PCT Filed: Aug. 18, 2011

(86) PCT No.: PCT/EP2011/004156
§ 371 (c)(1),
(2), (4) Date: Feb. 15, 2013

(87) PCT Pub. No.: WO2012/031672
PCT Pub. Date: Mar. 15, 2012

(65) Prior Publication Data
US 2013/0150624 A1    Jun. 13, 2013

(30) Foreign Application Priority Data
Sep. 11, 2010   (DE) .......................... 10 2010 045 142

(51) Int. Cl.
*C07C 209/26*  (2006.01)
(52) U.S. Cl.
USPC .......................................... 564/473

(58) Field of Classification Search
USPC .......................................... 564/473
See application file for complete search history.

(56) References Cited

U.S. PATENT DOCUMENTS 5,475,141 A *  12/1995  Kos et al. .................. 564/473
2008/0227632 A1   9/2008  Renken et al.

FOREIGN PATENT DOCUMENTS

DE           936211          12/1955
DE       19935448 A1          1/2001
EP        0628535 A1         12/1994

OTHER PUBLICATIONS

International Preliminary Report on Patentability and Written Opinion, Mar. 21, 2013.
Moller et al., Amine durch Reduktion, Houben-Weyl Methoden der organischen Chemie, 4th Edition, 1957, p. 602 ff., vol. XI/1, Georg Thieme Verlag, Stuttgart.

* cited by examiner

*Primary Examiner* — Brian J Davis
(74) *Attorney, Agent, or Firm* — Michael W. Farrell

(57) ABSTRACT

A continuous process for producing primary aliphatic amines having 9 to 18 carbon atoms by reaction of corresponding aliphatic aldehydes with ammonia and hydrogen in the presence of a hydrogenation catalyst in the liquid phase, characterized in that the reaction is carried out solventlessly at a molar ratio of aliphatic aldehyde:ammonia of at least 1:30, at a temperature of 100 to 200° C. and at a pressure of 6 to 11 MPa.

15 Claims, 1 Drawing Sheet

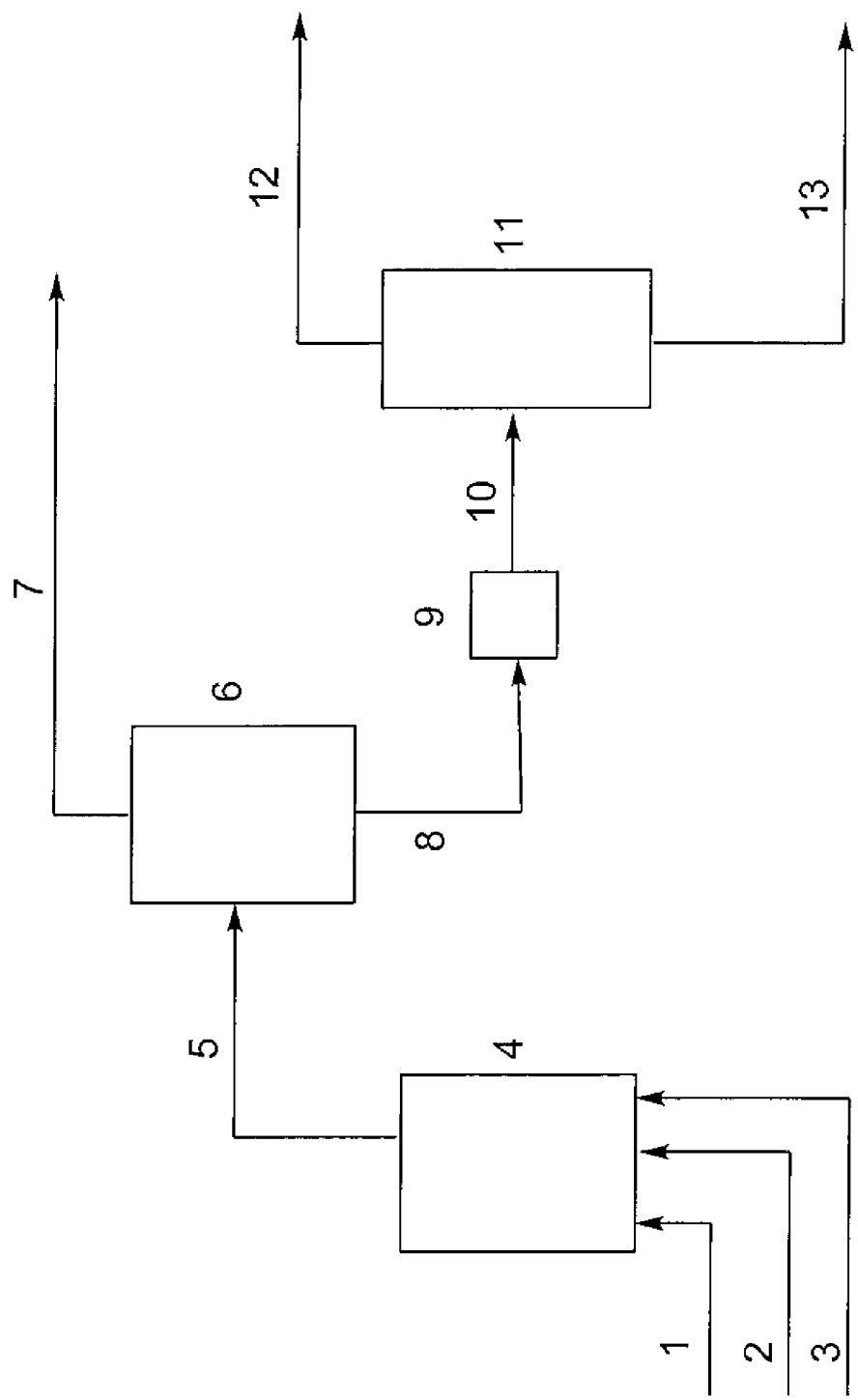

METHOD FOR PRODUCING PRIMARY ALIPHATIC AMINES FROM ALDEHYDES

CLAIM FOR PRIORITY

This application is a national phase application of PCT/EP2011/004156 FILED Aug. 18, 2011 which was based on application DE 10 2010 045 142.8 filed Sep. 11, 2010. The priorities of PCT/EP2011/004156 and DE 10 2010 045 142.8 are hereby claimed and their disclosures incorporated herein by reference.

TECHNICAL FIELD

The present invention relates to a process for obtaining aliphatic amines from aldehydes.

BACKGROUND

Aliphatic amines are important organic intermediates which are produced on a large industrial scale. They are further processed for the production of agrochemicals or dyes for example, or they are used in surface-active formulations, as a corrosion inhibitor in lubricants or as auxiliaries in the paper, textile and rubber industries.

It is known to produce primary aliphatic amines from aldehydes and ammonia with hydrogen over a catalyst. This reaction is also known as a reductive amination. Amine formation can be described by the following reaction stages:

  (1)

  (2)

The first reaction stage eliminates water to produce an imine, which is subsequently subjected to a catalytic hydrogenation in a second reaction stage.

However, unwanted secondary reactions also occur. First, the feed aldehydes may become directly hydrogenated to the alcohol. Secondly, the feed aldehyde may undergo an aldol condensation in the basic medium and primary amine which has already been formed can react with the feed aldehyde via the azomethine intermediate to form a secondary amine which can then further react in a similar fashion to form a tertiary amine. Moreover, the aldol condensation products contain reactive groups which can combine with the nitrogenous compounds to form comparatively high-boiling condensation products. To improve selectivity in the direction of the primary aliphatic amines and to restrain the formation of high-boiling by-products, various measures have been proposed in the prior art, for example using excess ammonia or a solvent when it is likely that the reaction mixture will become inhomogeneous as a result of the water formed (Houben-Weyl, Methoden der organischen Chemie, 4th Edition, Georg Thieme Verlag Stuttgart, Volume XI/1, p. 602 ff.).

DE 936211 describes a liquid-phase process for producing primary aliphatic amines. In this process, the aldehyde to be reacted is first mixed with ammonia at temperatures below 0° C. Optionally, the aldehydes are diluted with a low-boiling alcohol, for example methanol. This mixture is then catalytically hydrogenated, for example over a cobalt or nickel catalyst, at elevated temperature and pressure in the upflow or downflow mode.

In DE 199 35 448 A1, a mixture of methanol and ammonia is admixed with Raney nickel and hydrogen and heated to reaction temperature. The aldehyde is then added. After the reaction has ended, the batch is depressurized to evaporate methanol and ammonia. The primary aliphatic amine left behind is then further reacted.

EP 0 628 535 A1 discloses first mixing the aldehyde with a diluent, for example methanol or water, at not more than 5° C. to suppress hemiacetal or hydrate formation. A separate reaction vessel is initially charged with ammonia, hydrogen and nickel catalyst at elevated temperature and pressure, liquid ammonia being present in the reaction vessel. The cooled mixture of aldehyde and diluent is introduced into the reaction vessel while stirring. After the reaction has ended, the reaction mixture is filtered through a frit and the crude mixture freed of the catalyst is worked up. The known process teaches the use of a high molar excess of ammonia. At least 15 and preferably from 20 to 50 mol of ammonia are used per mole of aliphatic aldehyde.

In the process of US 2008/0227632 A1 the reductive amination of alcohols, aldehydes or ketones is carried out in the presence of a catalyst which, in addition to nickel, copper and chromium, additionally contains tin as an active metal. The addition of tin proves to be advantageous for restraining the formation of hydrogenated by-products. The known process is particularly useful for aminating mono- or polyfunctional alcohols, for example ethylene glycol, diethylene glycol or triethylene glycol.

In addition to these single-stage processes, the prior art also features two-stage processes wherein the aliphatic aldehyde and excess ammonia initially combine in the presence of an imination catalyst to form the imine intermediate which is subsequently converted with hydrogen into the primary aliphatic amine by using a hydrogenation catalyst. In EP 0 816 323 A2, the imination catalyst used in this two-stage procedure is an organopolysiloxane comprising sulphonate groups. The subsequent hydrogenation is carried out in the presence of, for example, cobalt-, nickel- or ruthenium-containing catalysts.

Existing single-stage processes either utilize a solvent or diluent, or require pre-mixing of the feed components with cooling. The use of a solvent or diluent necessitates specific removal from the reaction mixture as well as additional logistical measures, such as recycling and storekeeping. Precions reactor capacity is occupied and plant throughput reduced. Pre-mixing the feed components with cooling and maintaining low temperatures in the mixture before entry into the reactor represents an additional technical inconvenience.

It is an object of the present invention to provide a process for producing primary aliphatic amines which is technically convenient and provides the desired primary aliphatic amines with high selectivity. More particularly, the formation of high-boiling by-products shall be restrained as far as possible.

SUMMARY OF INVENTION

The present invention accordingly provides a continuous process for producing primary aliphatic amines having 9 to 18 carbon atoms by reaction of corresponding aliphatic aldehydes with ammonia and hydrogen in the presence of a hydrogenation catalyst in the liquid phase. The process is characterized in that the reaction is carried out solventlessly at a molar ratio of aliphatic aldehyde:ammonia of at least 1:30, at a temperature of 100 to 200° C. and at a pressure of 6 to 11 MPa.

Surprisingly, the solventless process suppress the formation of selectivity-reducing high boilers to below 10% by weight in the reaction product provided specific settings are used for the reaction conditions in the continuous process. Separate pre-mixing of the ammonia and aliphatic aldehyde feeds with cooling is not required. The feed materials are fed separately but concurrently into the amination reactor directly from their reservoir vessels without further apparatus measures.

BRIEF DESCRIPTION OF DRAWINGS

The invention is described in detail below with reference to the drawing wherein:

FIG. 1 is a schematic diagram illustrating operation of the inventive process for manufacturing primary aliphatic amines.

DETAILED DESCRIPTION

The invention is described in detail below in connection with the FIGURE for purposes of illustration, only. The invention is defined in the appended claims. Terminology used throughout the specification and claims herein are given their ordinary meanings, unless otherwise specifically indicated.

Solventless and solventlessly herein are to be understood as meaning that the active addition of a solvent or diluent is dispensed with. However, small amounts of secondary constituents can be present in the feed materials, for example residual alcohol in the feed aldehydes which is left over from their production process and has solvent or diluent properties. Nor does the water formed during the reaction come within the term solvent or diluent, even though it acts like a solvent in relation to ammonia.

At least 30 mol of ammonia, preferably at least 35 mol and more particularly from 37 to 45 mol of ammonia are used per mole of aliphatic aldehyde. Although the large excess of ammonia does lead to a dilution effect and thereby counteracts the formation of high boilers, the high proportion of the basic compound should ensure nonetheless that the aldehyde condensation proceeds to an appreciable extent, particularly since no added solvent or diluent is present according to the procedure of the present invention. To achieve economically acceptable yields of primary aliphatic amines, it is essential to use at least 30 mol of ammonia per mole of aliphatic aldehyde. If the amount of ammonia used is even minimally below this critical value a significant increase in high-boiling by-products will be observed.

Without wishing to speculate on the reaction mechanism, it is believed that at the high ammonia excess under the temperature and pressure conditions to be set, the aliphatic aldehyde is saturated with ammonia and is driven through the amination reactor as an ammonia-saturated stream of liquid. The liquid present is believed to exert a washing effect on the surface of the hydrogenation catalyst whereby surficial deposits can be removed from the hydrogenation catalyst. The performance of the hydrogenation catalyst is thus maintained throughout the on-stream time and the imine initially formed is immediately hydrogenated to the primary aliphatic amine. As hydrogenation performance decreases, the imine concentration in the reactor can rise and retrocleavage to the aldehyde then risks the formation of high-boiler aldehyde condensation products.

The reaction of the aliphatic aldehyde with ammonia in the presence of hydrogen over the hydrogenation catalyst takes place at temperatures of 100 to 200° C., preferably of 100 to 170° C. and more particularly of 120 to 150° C. At 170° C. or higher and particularly at 200° C. or higher an increase in high-boiler formation and hence decreased selectivity is observed, while the reaction rate decreases distinctly at temperatures below 100° C. The reaction pressure is in the range from to 11 MPa and preferably in the range from 7 to 9 MPa, and is made up essentially of the partial pressures of hydrogen and ammonia. Since supercritical conditions are not reached for ammonia, a liquid phase of ammonia-saturated feed aldehyde is present in the amination reactor alongside gaseous ammonia. At the same time, the stream of liquid driven through the amination reactor can act as a rinsing agent for the hydrogenation catalyst and clean the catalyst surface.

The hydrogenation catalysts used are customary catalysts used in the reductive amination of carbonyl compounds and containing at least one metal of transition groups 8 to 11 of the periodic table, such as nickel, cobalt, platinum, palladium, iron, rhodium or copper. Nickel or cobalt catalysts are particularly preferred. In addition to unsupported catalysts, such as Raney nickel or Raney cobalt, it is also possible to use supported catalysts. Supported catalysts generally contain the catalytically active metal in an amount of about 5% to 70% by weight, preferably about 10% to about 65% by weight and more particularly about 20% to 60% by weight, all based on the total weight of the hydrogenation catalyst. Any conventional catalyst support materials can be used, for example aluminium oxide, aluminium oxide hydrates in their various forms, silicon dioxide, polysilicic acids (silica gels) including kieselguhr, kiesel xerogels, magnesium oxide, zinc oxide, zirconium oxide and activated carbon. In addition to the main components, catalytically active metal and support material, the hydrogenation catalysts may further contain minor amounts of added substances used, for example, to improve their hydrogenation activity and/or their on-stream life and/or their selectivity. Added substances of this type are known; they include for example the oxides of calcium, of barium, of zinc, of aluminium, of zirconium and of chromium. They are generally added to the hydrogenation catalyst in a proportion of altogether 0.1% to 30% by weight, based on the total weight of the hydrogenation catalyst. Nickel has proved to be the preferred catalytically active metal. More particularly, nickel catalysts on kieselguhr as support material with chromium as added substance are suitable for the amination process of the present invention. A nickel catalysts containing 20% to 60% by weight of nickel, from 20% to 70% by weight of kieselguhr and from 10% to 20% by weight of chromium, all based on the total weight of the hydrogenation catalyst and optionally fillers making up the balance to 100% by weight, is very particularly suitable.

The reductive amination is carried out in the liquid phase, for example over fixed-bed catalysts in the downflow mode or upflow mode and also by stirring using suspension hydrogenation. Aliphatic aldehyde and ammonia are fed to the amination reactor separately but concurrently from their reservoir vessels in addition to hydrogen.

Preferably, the continuous reductive amination in liquid phase is carried out in a tubular reactor over fixed hydrogenation catalysts. A tubular reactor is also to be understood as meaning a bundle of multiple tubes connected in a close parallel arrangement. The tubular reactors used may likewise contain packing elements or internals, for example Raschig rings, saddles, Pall rings, filter plates or column trays, and also optionally stirring devices. In a particularly preferred embodiment, however, the reductive amination is carried out in a tubular reactor without internals, using a loose bed of hydrogenation catalyst.

A suspension hydrogenation is less preferable, since the operation of tubular devices in the amination reactor under reaction pressure requires special safety measures. Moreover, removing the hydrogenation catalyst suspended in the reaction solution, via filtering devices for example, is associated with additional operations.

The continuous process is advantageously run at a V/Vh catalyst space velocity, expressed in terms of throughput volume of aliphatic aldehyde per catalyst volume per time, of 0.02-0.50 h$^{-1}$ and preferably 0.05-0.30 h$^{-1}$. A higher space velocity of the aliphatic aldehyde over the hydrogenation catalyst must be avoided, or otherwise the reductive amination will no longer go to completion and, owing to the high residual aldehyde content, increased formation of high-boiling by-products is observed.

When throughputs are too low per unit time, plant capacity is not fully utilized.

The reductive amination preferably utilizes pure hydrogen as a starting compound in addition to ammonia. In addition to pure hydrogen, however, it is also possible to use mixtures containing free hydrogen and also constituents which are inert under the conditions of the reductive amination.

The aliphatic aldehydes to be reacted by the process of the present invention contain 9 to 18 carbon atoms in the molecule, preferably 9 to 15 and more preferably 13 to 15. The origin of the aliphatic aldehydes is not restricted to particular processes of production.

Owing to their ready availability, aldehydes obtained by the oxo or hydroformylation process, i.e. by reaction of $C_8$-$C_{17}$ olefins with carbon monoxide and hydrogen, are preferred while not only straight-chain but also branched olefins, for example olefin oligomers such as tripropylene or tetrapropylene, can be used as starting materials for the hydroformylation reaction. Useful aliphatic aldehydes include not only straight-chain n- but also branched-chain iso-aldehydes either in pure form or as a mixture with isomeric aldehydes of the same number of carbon atoms. Mixtures of aliphatic aldehydes having different numbers of carbon atoms can also be used. The process of the present invention is particularly useful for converting aliphatic aldehydes having 9 to 15 carbon atoms into the corresponding primary aliphatic amines, for example nonanal, decanal, undecanal, dodecanal, tridecanal, tetradecanal or pentadecanal or mixtures thereof. The corresponding aldehydes can be used as straight-chain compounds, as branched structural isomers or in a mixture of straight-chain and branched structural isomers, even with different numbers of carbon atoms. The mixture of straight-chain n- and branched-chain iso-aldehydes containing 13 and 15 carbon atoms in the molecule is very particularly useful for the amination process of the present invention.

The reaction mixture removed from the amination reactor is passed into a high-pressure separator where a gaseous phase and a liquid phase are formed. The gaseous phase contains essentially ammonia and hydrogen and also small amounts of water of reaction, and is removed. The liquid phase obtained is depressurized to atmospheric via a level controller, and flows into a reservoir container. In the course of the depressurizing operation, ammonia and hydrogen dissolved in the liquid phase come out of the liquid phase and are moved from the reservoir container as depressurization off-gas. Ammonia can be recovered from the removed off-gas of the high-pressure separator and from the depressurization off-gas, and returned back into the reductive process of amination.

Residual amounts of ammonia and the water of reaction are subsequently removed from the liquid phase collected in the reservoir container. The primary aliphatic amine obtained is subsequently purified in a conventional manner, by distillation for example, to on-spec product.

The process according to the present invention converts aliphatic aldehydes at high conversion and selectivity into the corresponding primary aliphatic amines. The level of high-boiling by-products, as determined by gas chromatography, in the crude product obtained after removal of ammonia and water of reaction formed is below 10%.

The process of the present invention will now be more particularly elucidated with reference to the in-principle scheme of FIG. 1. However, the process of the present invention is not restricted to the embodiment depicted in the drawing.

Line (1) introduces ammonia, line (2) hydrogen and line (3) aliphatic aldehyde in a continuous manner into the amination reactor (4) packed with the hydrogenation catalyst. The reactor effluent exits via line (5) into a high-pressure separator (6) where a gaseous phase and liquid phase are formed. The gas phase from the high-pressure separator (6) is removed via line (7). Ammonia is recovered from the removed gas phase, which consists essentially of ammonia and hydrogen and contains small amounts of water of reaction, and is returned (not shown in FIG. 1) back into the process via line (1). The liquid phase obtained in the high-pressure separator (6) is removed via line (8), depressurized to atmospheric via a level controller (9) and passes via line (10) at atmospheric pressure into the reservoir container (11). The gaseous fractions formed in the course of the depressurizing operation, which are essentially residual amounts of dissolved ammonia and hydrogen, are removed from the system via line (12). Optionally, ammonia can be recovered from the removed stream and returned (not shown in FIG. 1) back into the amination reactor (4) via line (1) together with fresh ammonia. The devolatilized liquid phase is removed via line (13) and subsequently worked up distillatively in a conventional manner (not shown in FIG. 1).

The process of the present invention will now be more particularly elucidated with reference to some examples, but it is not restricted to the embodiment described.

Experimental Set-Up

The reductive amination was carried out over a commercial kieselguhr-supported nickel catalyst with chromium as added substance in a tubular reactor in the upflow mode. The catalyst volume was 1.95 liters. The aliphatic aldehyde used was a mixture of straight-chain n- and branched-chain iso-$C_{13}$ and $C_{15}$ aldehydes. This feed mixture, ammonia and hydrogen were fed separately but concurrently to the bottom end of the tubular reactor in a continuous manner. The reaction product was withdrawn at the top of the tubular reactor and passed into a high-pressure separator. The generated liquid was depressurized to atmospheric via a level controller and passed into an atmospheric reservoir vessel. The organic crude product obtained was subsequently analysed by gas chromatography.

The reaction conditions and the continuous feed of the starting materials were set in accordance with the conditions of Table 1 below. Table 1 likewise reports the composition of the organic product, without ammonia and water, determined by gas chromatography (in %).

The aliphatic aldehyde mixture used for the experiments had the following typical composition (determined by gas chromatography, reported in percent):

| | |
|---|---|
| $C_{12}$ and $C_{14}$ HC | 1.9 |
| n-/i-$C_{13}$ aldehyde | 63.3 |
| n-/i-$C_{15}$ aldehyde | 34.3 |
| After-run C26-C30 | 0.5 |

TABLE 1

Reductive amination of an n-/iso-$C_{13}$/$C_{15}$ aldehyde mixture and gas chromatography analyses of resulting crude primary aliphatic amine in % (without ammonia and water)

| Catalyst amount ml/g | Example 1 1950 ml/ 1095 g | Example 2 1950 ml/ 1095 g | Example 3 1950 ml/ 1095 g |
|---|---|---|---|
| Pressure MPa | 8 | 8 | 8 |
| Catalyst temperature ° C. | 140 | 120 | 120 |
| Hydrogen feed l/h | 200 | 200 | 211 |
| Aldehyde feed g/h | 414 | 103 | 300 |
| Ammonia feed g/h | 1500 | 1505 | 1500 |
| V/Vh based on aldehyde 1/h | 0.22 | 0.05 | 0.16 |
| Product analysis | | | |
| $C_{12}$ and $C_{14}$ hydrocarbon | 1.7 | 1.7 | 1.8 |
| n/i-$C_{13}$ amine | 61.0 | 60.4 | 61.9 |
| n/i-$C_{15}$ amine | 32.3 | 33.8 | 33.5 |
| After-run C26-C30 | 5.0 | 4.1 | 2.8 |

As evidenced by the examples according to the present invention, the level of high-boiling by-products in the crude primary aliphatic amine can be reduced to distinctly below 10%. The process of the present invention provides primary aliphatic amines with high selectivity at minimal technical inconvenience.

The invention claimed is:

1. Continuous process for producing primary aliphatic amines having 9 to 18 carbon atoms by reaction of corresponding aliphatic aldehydes with ammonia and hydrogen in the presence of a hydrogenation catalyst in the liquid phase, characterized in that the reaction is carried out solventlessly at a molar ratio of aliphatic aldehyde:ammonia of at least 1:30, at a temperature of 100 to 200° C. and at a pressure of 6 to 11 MPa.

2. Process according to claim 1, characterized in that the molar ratio of aliphatic aldehyde:ammonia is at least 1:35.

3. Process according to claim 1, characterized in that the reaction is carried out at a temperature of 100 to 170° C.

4. Process according to claim 3, characterized in that the reaction is carried out at a temperature of 120 to 150° C.

5. Process according to claim 1, characterized in that the reaction is carried out at a pressure of 7 to 9 MPa.

6. Process according to claim 1, characterized in that the aliphatic aldehydes to be reacted contain 9 to 15 carbon atoms in the molecule.

7. Process according to claim 1, characterized in that the hydrogenation catalyst contains at least nickel, cobalt, platinum, palladium, iron, rhodium or copper.

8. Process according to claim 1, characterized in that the hydrogenation catalyst contains a support material.

9. Process according to claim 1, characterized in that the hydrogenation catalyst contains oxides of calcium, of barium, of zinc, of aluminium, of zirconium, of chromium, or mixtures thereof, as added substances.

10. Process according to claim 1, characterized in that the hydrogenation catalyst used is a nickel catalyst containing 20% to 60% by weight of nickel, from 20% to 70% by weight of kieselguhr and from 10% to 20% by weight of chromium, all based on the total weight of the hydrogenation catalyst and optionally fillers making up the balance to 100% by weight.

11. Process according to claim 1, characterized in that the aliphatic aldehydes to be reacted are used as a mixture of aliphatic aldehydes having different numbers of carbon atoms.

12. Process according to claim 1, characterized in that a mixture of straight-chain n- and branched-chain iso-aldehydes containing 13 and 15 carbon atoms in the molecule is used.

13. Process according to claim 1, characterized in that the molar ratio of aliphatic aldehyde:ammonia is in the range from 1.37 to 1.45.

14. Process according to claim 1, characterized in that the aliphatic aldehydes to be reacted contain 13 to 15 carbon atoms in the molecule.

15. Continuous process for producing primary aliphatic amines having 9 to 18 carbon atoms by reaction of corresponding aliphatic aldehydes with ammonia and hydrogen in the presence of a hydrogenation catalyst in the liquid phase, characterized in that the reaction is carried out solventlessly at a molar ratio of aliphatic aldehyde:ammonia of at least 1:30, at a temperature of 100 to 170° C. and at a pressure of 7 to 9 MPa in the presence of a hydrogenation catalyst comprising at least nickel, cobalt, platinum, palladium, iron, rhodium or copper.

* * * * *